United States Patent
Buchanan et al.

[11] 3,980,668
[45] Sept. 14, 1976

[54] ANTI-ARRHYTHIMIC 5-ENDO-(3-INDOLECARBONYLOXY)-N-[AMINO-(LOWER)ALKYL]BICYCLO[2,2,1]HEPTANE-2,3-DI-ENDO-CARBOXYLIC ACID IMIDES

[75] Inventors: Ronald Leslie Buchanan, Fayetteville, N.Y.; Alex Michael Jelenevsky, Greensboro, N.C.

[73] Assignee: Bristol-Myers Company, New York, N.Y.

[22] Filed: July 10, 1975

[21] Appl. No.: 594,918

Related U.S. Application Data

[63] Continuation-in-part of Ser. No. 507,029, Sept. 18, 1974, abandoned.

[52] U.S. Cl. .................... 260/326 C; 260/247.2 A; 260/268 TR; 260/293.61; 260/343.3 R; 424/248; 424/250; 424/267; 424/274
[51] Int. Cl.[2] ........................................ C07D 209/76
[58] Field of Search ................ 260/326 C, 247.2 A, 260/268 TR, 293.61, 326 C

[56] References Cited
UNITED STATES PATENTS

| | | | |
|---|---|---|---|
| 3,850,921 | 11/1974 | Matno et al. ..................... | 260/326 C |
| 3,850,922 | 11/1974 | Matno et al. ..................... | 260/326 C |

*Primary Examiner*—Lewis Gotts
*Assistant Examiner*—S. P. Williams
*Attorney, Agent, or Firm*—Robert E. Havranek

[57] ABSTRACT

A series of 5-endo-(3-indolecarbonyloxy)-N-[amino-(lower)alkyl]bicyclo[2.2.1]heptane-2,3-di-endo-carboxylic acid imides having the formula

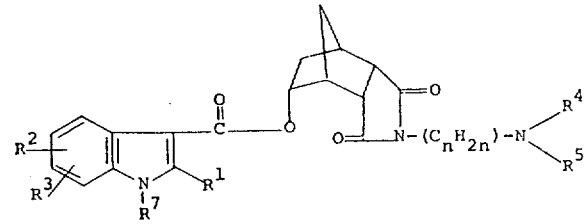

wherein $R^1$ is H, Cl, Br, F or (lower)alkyl, $R^7$ is H or methyl, $R^2$ and $R^3$ are alike or different and each is H, Cl, Br, F, (lower)alkyl, nitro, $CF_3$, OH or (lower)alkoxy, n is an integer of 2 to 4 inclusive and $R^4$ and $R^5$ are alike or different and each is H, (lower)alkyl or when taken together with the nitrogen a radical of the formula

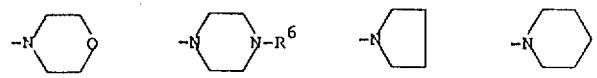

in which $R^6$ is (lower)alkyl; or a pharmaceutically acceptable acid addition salt thereof have been found to possess unique prophylactic and therapeutic activity as anti-arrhythmia agents. An example of such a compound possessing excellent activity is 5-endo-(3-indolecarbonyloxy)-N-(3-dimethylaminopropyl)bicyclo-[2.2.1]heptane-2,3-di-endo-carboxylic acid imide hydrochloride.

18 Claims, No Drawings

ANTI-ARRHYTHIMIC 5-ENDO-(3-INDOLECARBONYLOXY)-N-[AMINO-(LOWER)ALKYL]BICYCLO[2,2,1]HEPTANE-2,3-DI-ENDO-CARBOXYLIC ACID IMIDES

CROSS-REFERENCE TO RELATED APPLICATIONS

This application is a continuation-in-part of a copending application Ser. No. 507,029, filed Sept. 18, 1974, and now abandoned.

BACKGROUND OF THE INVENTION

1. Field of the Invention

This invention relates to a novel series of 5-endo-(3-indolecarbonyloxy)-[amino(lower)alkyl]-bicyclo[2.2.1]heptane-2,3-di-endo-carboxylic acid imides possessing anti-arrhythmic and/or anti-fibrillatory activity.

2. Description of the Prior Art

A. British Pat. No. 1,042,840 describes compounds having the formula

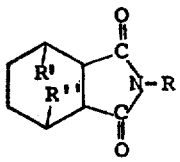

in which each of R' and R'' represent hydrogen, or together an alkylene group having 1 or 2 carbon atoms, and R represents an alkyl group having 6 to 18, preferably 8 to 12 carbon atoms in a straight chain as having particularly advantageous properties as functional fluids.

B. U.S. Pat. No. 2,393,999 describes the compounds having the formula

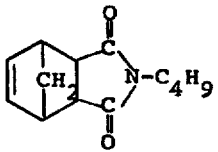

as being an effective insecticide.

C. U.S. Pat. No. 2,424,220 describes the compound having the formula

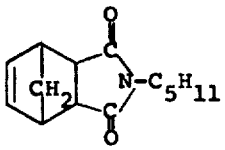

as being an effective insecticide.

D. U.S. Pat. No. 2,462,835 describes the compound having the formula

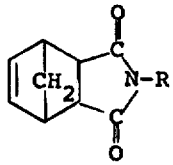

in which R is alkyl, alkene, aryl, substituted aryl, alkynyl, etc. as insecticides.

E. Culberson and Wilder, Jr., J. Org. Chem., 25, pp. 1358–62 (1960) report the preparation of compounds having the formula

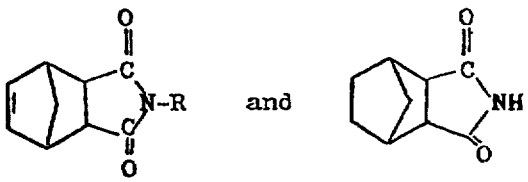

in which R is $CH_3$, $C_6H_{13}$ or hydrogen.

F. Rice, Reide and Grogan, J. Org. Chem., 19, pp. 884–893 (1954) report the preparation of compounds of the formula

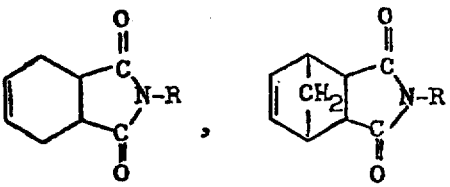

and

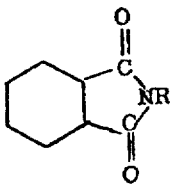

in which R is alkyl and their subsequent reduction with lithium aluminum hydride.

G. Worral, J. Am. Chem. Soc., 82, pp. 5707–5711 (1960) report the preparation of compounds having the formula

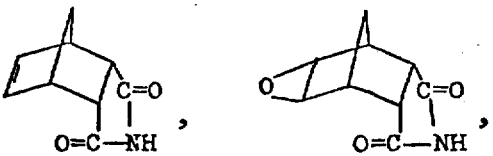

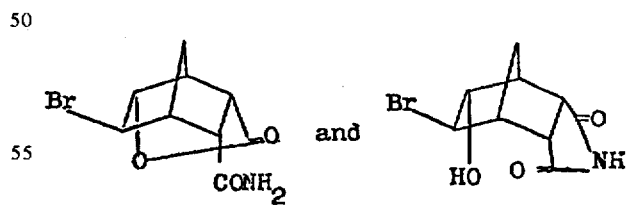

H. German Auslegeschrift No. 1,179,205 reports the preparation of compounds having the formula

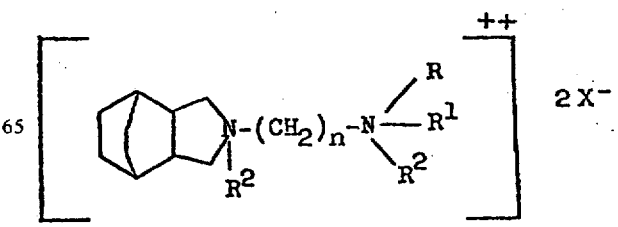

in which the bicyclo[2.2.2]octane ring system is saturated and/or substituted, R and R¹ are alkyl or alkenyl groups of 1 to 5 carbon atoms, or when combined with the nitrogen a heterocyclic ring. R² is a (lower)alkyl group, n is a number of 2 to 5 and X a halogen anion. The quaternary compounds are described as having therapeutic properties in the treatment of cardiovascular disease, specifically high blood pressure.

I. U.S. Pat. No. 3,850,922 disclosed and claims the compounds having the formula

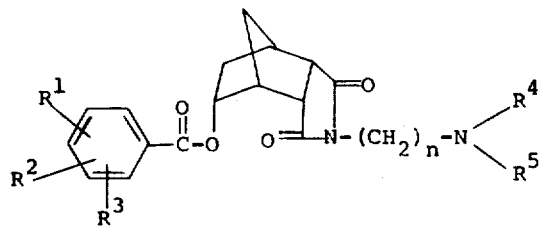

wherein R¹, R² or R³ is H, Cl, Br, F, (lower)alkyl, nitro, OH or (lower)alkoxy, n is an integer of 2 to 4 inclusive and R⁴ or R⁵ is H, (lower)alkyl or when taken together with the nitrogen a radical of the formula

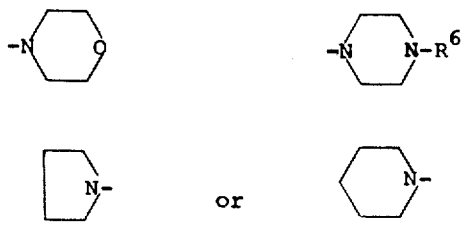

in which R⁶ is (lower)alkyl; or a pharmaceutically acceptable acid addition salt thereof as anti-arrhythmic agents.

J. U.S. Pat. No. 3,850,921 discloses and claims the compounds having the formula

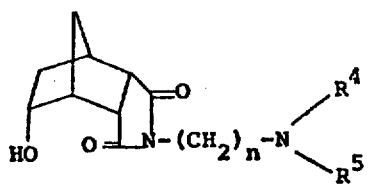

wherein n is an integer of 2 to 4 inclusive and R⁴ and R⁵ are H, (lower)alkyl or when taken together with the nitrogen a radical of the formula

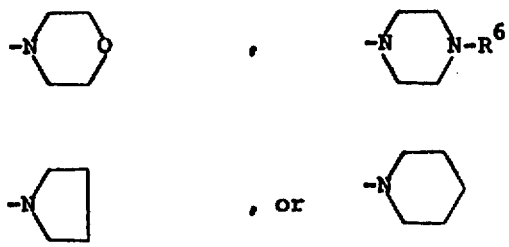

in which R⁶ is (lower)alkyl; or an acid addition salt thereof as intermediates in the preparation of the anti-arrhythmia compounds found in U.S. Pat. No. 3,850,922 supra.

SUMMARY OF THE INVENTION

Compounds having the formula

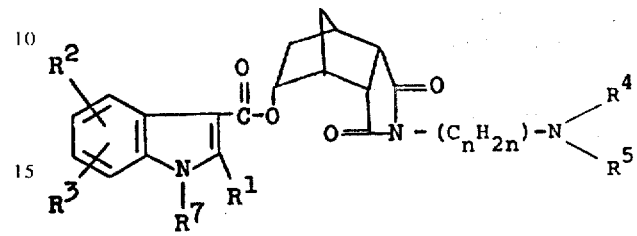

wherein R⁷ is hydrogen or methyl, R¹ is chloro, bromo, fluoro, hydrogen or (lower)alkyl and R² and R³ are alike or different and each is H, Cl, Br, F, (lower)alkyl, nitro, CF₃, OH or (lower)alkoxy, n is an integer of 2 to 4 inclusive and R⁴ and R⁵ are alike or different and each is H, (lower)alkyl or when taken together with the nitrogen a radical of the formula

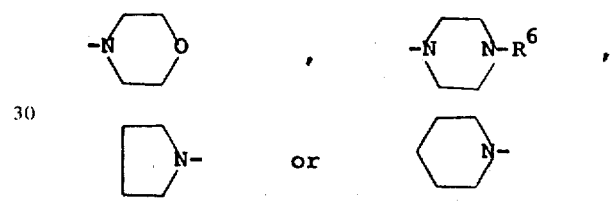

in which R⁶ is (lower)alkyl; or a pharmaceutically acceptable acid addition salt thereof are anti-arrhythmic agents.

Cardiac arrhythmia, a phenomenon commonly associated with coronary heart disease or myocardial infarction, is an affliction not uncommon in humans, especially the elderly. The mechanism of caradiac arrhythmia is suspected to be caused by an abnormal "focus" in the ventricle of the heart which sends out (fires) nerve signals more rapidly than required for the normal beating of the heart. Uncontrolled arrhythmia can lead to fibrillation which results in death.

It has been discovered that the series of compounds herein designated 5-endo-(3-indolecarbonyloxy)-N-[amino-(lower)alkyl]-bicyclo[2.2.1]heptane-2,3-di-endo-carboxylic acid imides having the formula

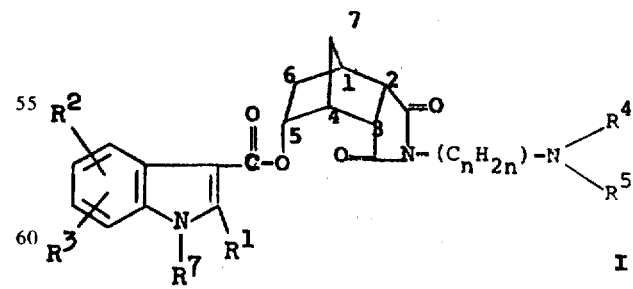

I wherein R⁷ is hydrogen or methyl, R¹ is Cl, Br, F, hydrogen or (lower)alkyl and R² and R³ are alike or different and each is H, Cl, Br, F, (lower)alkyl, nitro, OH or (lower)alkoxy, n is an integer of 2 to 4 inclusive and $R^4$ and $R^5$ are alike or different and each is H, (lower)alkyl or when taken together with the nitrogen a radical of the formula

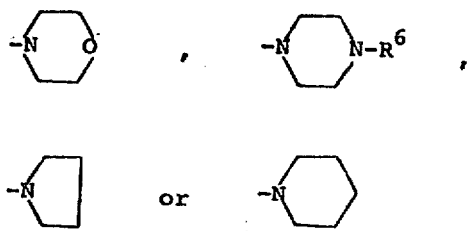

in which $R^6$ is (lower)alkyl; or a pharmaceutically acceptable acid addition salt thereof are useful therapeutic or prophylactic agents in the suppression of the abnormal ectopic beat.

Compound I can theoretically exist in several isomeric forms, namely:

A. endo-3-indolecarbonyloxy:endo-substituted imide;
B. exo-3-indolecarbonyloxy:exo-substituted imide (X);
C. endo-3-indolecarbonyloxy:exo-substituted imide; and
D. exo-3-indolecarbonyloxy:endo-substituted imide.

Furthermore, each of these isomers has two optical isomers; levorotatory and dextrorotatory.

The distinction between the isomers is determined by the relative position of the constituent bonds at positions 2, 3 and 5 of the bicyclo ring system.

When these bonds, i.e., the constituent bonds at positions 2, 3 and 5 are on the same side as the $C_7$ bridge, we have the exo-exo isomer. When these bonds, i.e., the constituent bonds at positions 2, 3 and 5 are on the opposite side of the $C_7$ bridge or alternatively within the cage formed by carbon atoms 2, 3, 5 and 6, then we have the endo-endo isomer. When the constituent bond at position 5 is on the same side as the $C_7$ bridge and the constituent bonds 2 and 3 are on the opposite side of the $C_7$ bridge, we have the endo-exo isomer. Illustrative of the exo-exo isomer is the compound having the formula

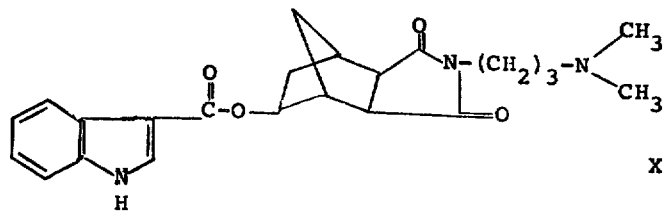

Illustrative of endo-endo is the compound of formula I.

The only isomers claimed in this invention are the endo-endo isomers as represented by compound I and the dextro- and levorotatory isomers thereof. The endo-endo isomers are inherently exclusively produced by the synthesis described herein.

The optical isomers of I can be separated and isolated by fractional crystallization of the diastereoisomeric salts formed, for instance, with (+) or (−)-tartaric acid or D-(+)camphor sulfonic acid.

Alternatively, and probably preferably, the optical isomers of compound I can be prepared by resolving compound III by the fractional cryrstallization of the diastereoisomeric salts formed, for instance, with (+) or (−) tartaric or D-(+) camphorsulfonic acid, followed by esterification to produce compound I.

For the purpose of this disclosure, the term "(lower)alkyl" is defined as an alkyl radical containing 1 to 6 carbon atoms. The alkyl radical can be branched or straight chained, e.g., n-propyl, isopropyl, etc. The representation $-(C_nH_{2n})-$ in which n is 2 to 4 is meant to include all variations of the radical, e.g., $-CH_2-CH_2-CH_2-$, $$-CH_2-\underset{\underset{CH_3}{|}}{CH}-, \quad -CH_2-\underset{\underset{CH_3}{|}}{CH}-CH_2-,$$

etc. The term "(lower)alkoxy" is an alkoxy radical containing 1 to 6 carbon atoms. The term "pharmaceutically acceptable acid addition salt" is defined to include all those inorganic and organic acid salts of the compounds of the instant invention, which salts are commonly used to produce nontoxic salts of medicinal agents containing amine functions. Illustrative examples would be those salts formed by mixing the compounds of formula I with hydrochloric, sulfuric, nitric, phosphoric, phosphorous, hydrobromic, maleic, malic, ascorbic, citric or tartaric, pamoic, lauric, stearic, palmitic, oleic, myristic, laurylsulfonic, naphthalenesulfonic, linoleic or linolenic acid, and the like.

The compounds of the instant invention are closely related to those disclosed and claimed in U.S. Pat. Nos. 3,850,922 and 3,850,921 in the names of our associates, Sadao Ohki and Ichiro Matuo.

The compounds of those applications are characterized by the following generic formula:

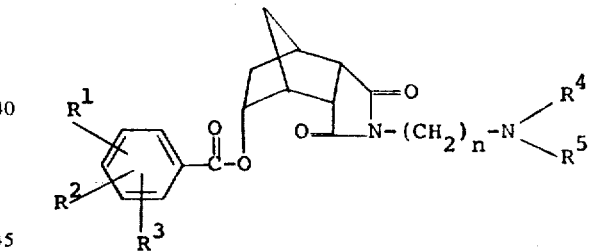

wherein $R^1$, $R^2$ or $R^3$ is H, Cl, Br, F, (lower)alkyl, nitro, OH or (lower)alkoxy, n is an integer of 2 to 4 inclusive and $R^4$ and $R^5$ are H, (lower)alkyl or when taken together with the nitrogen a radical of the formula

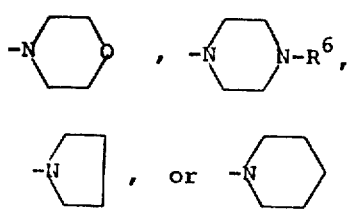

in which $R^6$ is (lower)alkyl.

As should be apparent, all the compounds of these applications are esters of 5-endo-hydroxy-N-[amino(-lower)alkyl]bicyclo[2.2.1]heptane-2,3-di-endo-carboxylic acid imide (III).

Subsequent to the filing of the above-identified applications, it was found that while those compounds exhibited excellent anti-arrhythmia properties of moderate to long duration in rats and mice, in particular the compound (+)-5-endo-benzoyloxy-(3-dimethylaminopropyl)-bicyclo[2.2.1]heptane-2,3-endo-dicarboxylic acid imide hydrochloride, the compound only possessed activity of short duration in humans due to a particular susceptibility to an esterase found in human serum. Apparently, the compound is rapidly hydrolyzed to an inert species, identified as compound IIIa.

On receipt of this knowledge, extensive effort was expended to discover compounds that would be resistent to this enzymatic hydrolysis. It was found that 3-indolecarbonyloxy esters were particularly resistent to the in vivo hydrolysis.

A preferred embodiment of the present invention is the compound having the formula

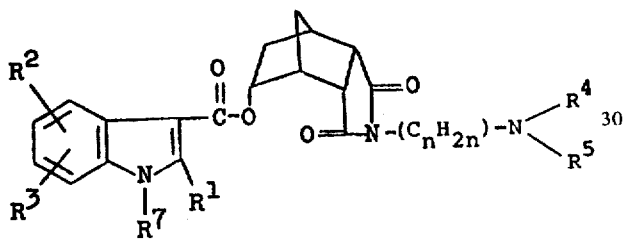

wherein $R^7$ is hydrogen or methyl, $R^1$ is Cl, Br, F, hydrogen or (Lower)alkyl and $R^2$ and $R^3$ are alike or different and each is H, Cl, Br, F, (lower)alkyl, nitro, $CF_3$, OH or (lower)alkoxy, n is an integer of 2 to 4 inclusive and $R^4$ and $R^5$ are alike or different and each is H, (lower)alkyl or when taken together with the nitrogen a radical of the formula

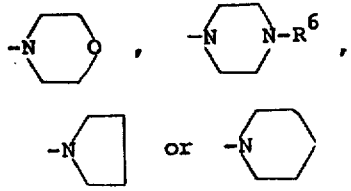

in which $R^6$ is (lower)alkyl; or a pharmaceutically acceptable acid addition salt thereof.

A preferred embodiment of the present invention is the compound having the formula

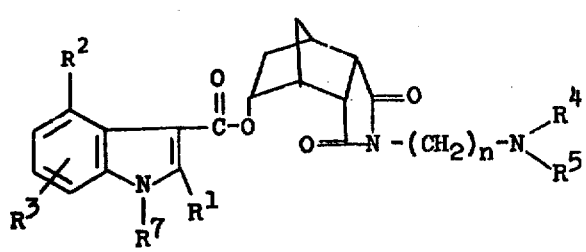

wherein $R^7$ is hydrogen or methyl, $R^1$ is Cl, Br, F, hydrogen or (lower)alkyl and $R^2$ and $R^3$ are alike or different and each is H, F, Cl, OH, Br, $CF_3$, (lower)alkoxy, or (lower)alkyl, n is an integer of 2 to 4 inclusive and $R^4$ and $R^5$ are alike or different and each is H, (lower)alkyl or when taken together with the nitrogen a radical of the formula

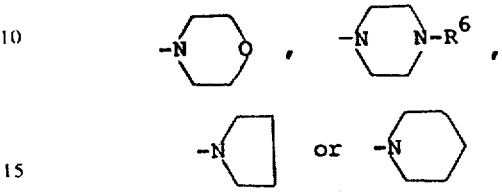

in which $R^6$ is (lower)alkyl; or a pharmaceutically acceptable acid addition salt thereof.

Another preferred embodiment of the present invention is the compound having the formula

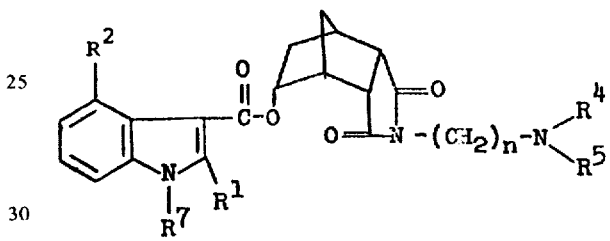

wherein $R^7$ is hydrogen or methyl, $R^1$ is Cl, Br, F, hydrogen or (lower)alkyl and $R^2$ is H, F, Cl, OH, Br, $CF_3$, (lower)alkoxy or (lower)alkyl, n is an integer of 2 to 4 inclusive and $R^4$ and $R^5$ are alike or different and each is H, (lower)alkyl or when taken together with the nitrogen a radical of the formula

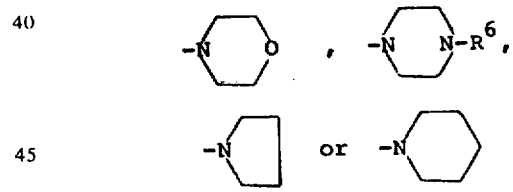

in which $R^6$ is (lower)alkyl; or a pharmaceutically acceptable acid addition salt thereof.

Another preferred embodiment of the present invention is the compound having the formula

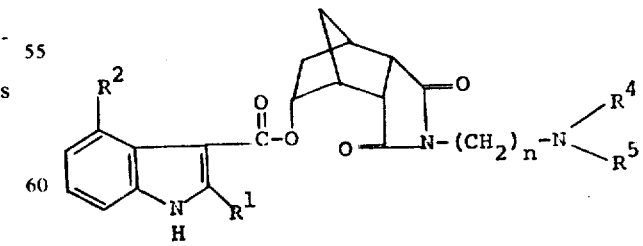

wherein $R^1$ and $R^2$ are alike or different and each is H, Cl, Br, F, or (lower)alkyl, and $R^2$ can also be $CF_3$, n is an integer of 2 to 4 inclusive and $R^4$ and $R^5$ are H, (lower)alkyl or when taken together with the nitrogen a radical of the formula

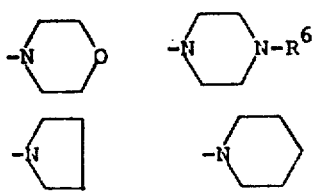

in which $R^6$ is (lower)alkyl; or a pharmaceutically acceptable acid addition salt thereof.

Another preferred embodiment of the present invention is the compound having the formula

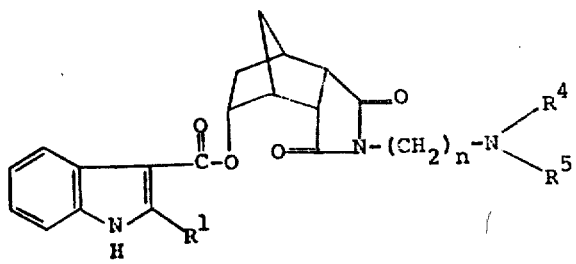

wherein $R^1$ is H, F, Cl, methoxy, ethoxy or n-propoxy, n is an integer of 2 to 4 inclusive and $R^4$ and $R^5$ are alike or different and each is H, (lower)alkyl or when taken together with the nitrogen a radical of the formula

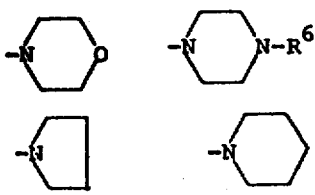

in which $R^6$ is (lower)alkyl; or a pharmaceutically acceptable acid addition salt thereof.

Another preferred embodiment of the present invention is the compound having the formula

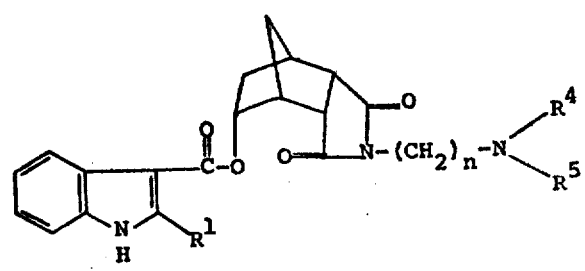

wherein $R^1$ is H, F, Cl, methoxy, ethoxy or n-propoxy, n is an integer of 2 to 4 inclusive and $R^4$ and $R^5$ are alike or different and each is H or (lower)alkyl; or a pharmaceutically acceptable acid addition salt thereof.

Another preferred embodiment of the present invention is the compound having the formula

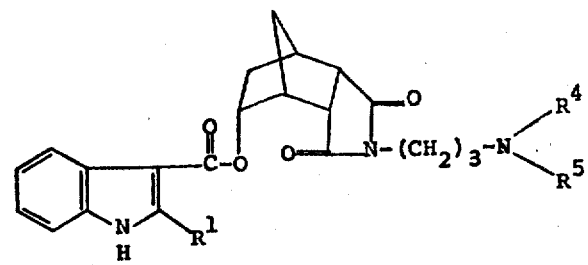

in which $R^1$ is H, Cl, methoxy, or ethoxy, and $R^4$ and $R^5$ are alike or different and are H or (lower)alkyl; or a pharmaceutically acceptable acid addition salt thereof.

A most preferred embodiment of the present invention is the compound having the formula

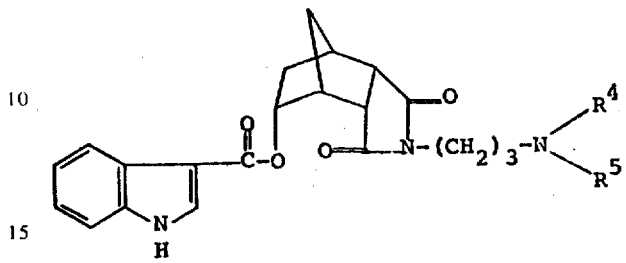

in which $R^4$ and $R^5$ are alike or different and each is H, methyl, ethyl or isopropyl; or a pharmaceutically acceptable acid addition salt thereof.

A most preferred embodiment of the present invention is the compound having the formula

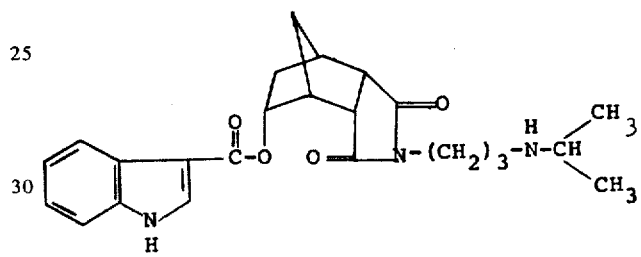

or the hydrochloride salt thereof.

The most preferred embodiment of the present invention is the compound having the formula

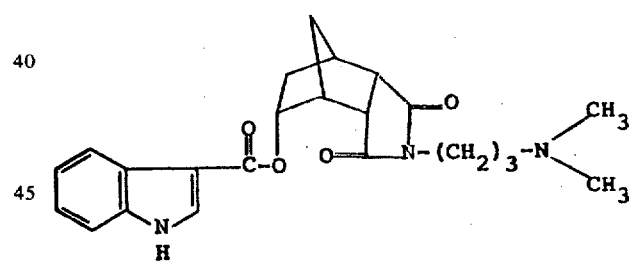

or the hydrochloride salt thereof.

Another preferred embodiment is the essentially pure dextrorotatory isomers of the compound I.

Still another preferred embodiment is the essentially pure levorotatory isomers of the compound I.

The objectives of the present invention have been achieved by the process of preparing the compounds having the formula

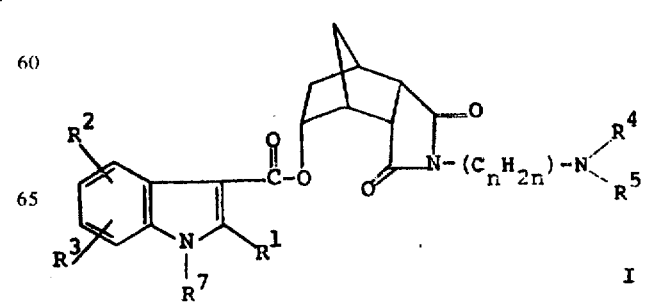

I wherein $R^7$ is H or methyl, $R^1$ is H, F, Cl, Br, or (lower-)alkyl, $R^2$ and $R^3$ are alike or different and each is H, Cl, Br, F, (lower)alkyl, nitro, OH or (lower)alkoxy, n is an integer of 2 to 4 inclusive and $R^4$ and $R^5$ are alike or different and each is H, (lower)alkyl or when taken together with the nitrogen a radical of the formula

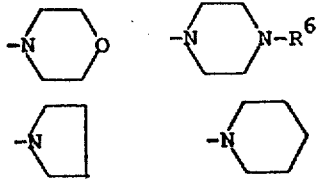

in which $R^6$ is (lower)alkyl; which process comprises the consecutive steps of A. treating a suspension of endo-cis-bicyclo[2.2.1]hept-5-ene-2,3-dicarboxylic anhydride or exo-cis-bicyclo[2.2.1]hept-5-ene-2,3-dicarboxylic anhydride in water, but preferably the endo-cis isomer, with excess concentrated sulfuric acid at a temperature in the range of 70°–95° C. to produce the endo-endo compound having the formula

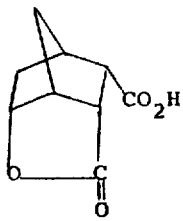
II

B. treating 1 mole of compound II with at least one mole of thionyl chloride or phosphorous trichloride at reflux temperature for at least 15 minutes and removing the excess thionyl chloride or phosphorous trichloride in vacuo to produce an oily residue IIa;

C. treating residue IIa with at least one mole of an amine having the formula

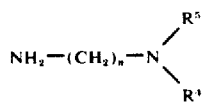

in which n is an integer of 2 to 4 inclusive, $R^4$ or $R^5$ are alike or different and each is H, (lower)alkyl or when both are taken with the nitrogen a radical of the formula

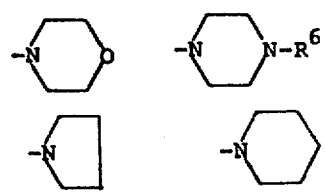

in which $R^6$ is (lower)alkyl; in an organic solvent, preferably selected from the group comprising benzene, toluene, xylene, and the like at about reflux temperatures for at least 30 minutes and removing the solvent in vacuo to produce an oily residue IIb;

D. treating residue IIb with at least one mole of potassium hydroxide in a mixture of a (lower)alkanol and water with the aid of heat, but preferably at reflux temperature for at least one hour to produce the compound having the formula

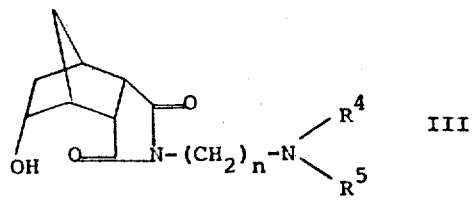
III in which n, $R^4$ and $R^5$ are as above, which may be resolved into its optical isomers if desired; and E. treating one mole of compound III with at least one mole of a 3-indolecarbonyl halide, or its chemical equivalent, having the formula

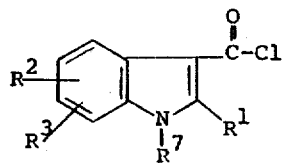

in which $R^1$, $R^2$, $R^7$ and $R^3$ are as defined above and X is chloro, bromo or iodo, but preferably chloro, in an organic solvent, preferably selected from the group consisting of benzene, toluene, xylene, pyridine, methylene chloride, chloroform or mixtures thereof, in a temperature range of 0° to 60°C., but preferably at about room temperature to yield compound I.

The compounds were tested in dogs for their reversion activity in ouabain-induced arrhythmia.

Anesthetized dogs were used for the production of ouabain-induced ventricular arrhythmias. The arrhythmia consisted of a nodal or ventricular tachycardia. The procedure used to establish the arrhythmia as well as the criteria employed to determine anti-arrhythmic activity generally was that employed by Lucchesi et al.[1]

Anti-arrhythmic activity of (±)-BL-4712A was determined by rapid intravenous injection and compared to lidocaine, disopyramide and aprindine. The average prolonged reversion doses are shown below:

| Compound | I.V. Reverting Dose, mg/kg* |
|---|---|
| (±)-BL-4712A | 0.62 ± 0.17 (N=5) |
| Lidocaine | 6.4 ± 1.4 (N=8) |
| Disopyramide | 4.5 ± 1.3 (N=6) |
| Aprindine | 2.46 ± 0.83 (N=5) |

*Values are means ± standard error, N = No. of animals.

The compounds were also tested for their reversion of ventricular arrhythmia due to coronary artery ligation in conscious dogs:

Multifocal ventricular ectopic rhythms were produced in dogs according to the coronary artery ligation method of Harris[2]. Approximately 24 hours after induction of the ventricular arrhythmia the test drugs were infused at a rate of 0.2 mg./kg./min. The approximate average doses necessary to product a 50% decrease in the number of ventricular ectopic beats, and to produce reversion of the ventricular arrhythmia are shown below. In contrast to 1 and 2, no reversion was observed with an intravenous infusion of lidocaine or quinidine in doses of up to 20 mg./kg.

| Compound | I.V. Dose Producing 50% Reduction in Ectopic Beats (mg./kg.) | I.V. Reverting Dose (mg./Kg.) |
|---|---|---|
| 1. (±)-BL-4712A | 1.8 (N=4) | 5-10 (N=4) |
| 2. Aprindine | 3.5 (N=3) | 10 (N=3) |
| 3. Lidocaine | >20 (N=5) | >20 (N=5) |
| 4. Quinidine | 10 (N=5) | >20 (N=5) |

*Values are means, N = No. of experiments.

Local anesthetic activity was determined by using the general method of Bulbring et al.[3], in conscious guinea pigs. Intradermal injections of lidocaine and (±)-BL-4712A were made on the back, and 30 minutes later, the animals were tested for their reaction to pain from stimuli applied with a hypodermic needle. The doses necessary to produce a 50% decrease in reaction to pain are shown below along with the confidence limits.

| Local Anesthetic Activity in Guinea Pigs | |
|---|---|
| Compound | $ED_{50}$ in mmoles of drug |
| (±)-BL-4712A | 24 (20–29) |
| lidocaine | 23 (16–32) |

References

1. Lucchesi, B. L. and H. F. Hardman: The influence of dichloroisoproterenol (DCI) and related compounds upon ouabain and acetylstrophanthidin induced cardiac arrhythmias. J. Pharmacol. Exp. Therap., 132:372, 1961.

2. Harris, A.S.: Delayed development of ventricular ectopic rhythms following experimental coronary occlusion. Circulation 1:1318, 1950.

3. Bulbring, E. and I. Wajda: Biological comparison of local anesthetics, J. Pharmacol Exp. Therap., 85:78, 1941.

All the compounds within the scope of the present invention possess anti-arrhythmic activity.

The compounds of the present invention are useful in the treatment of cardiac arrhythmia in mammals, including man, as prophylactic or therapeutic agents in doses in the range of 0.25 mg. to 3.0 mg./kg. up to 3 or 4 times a day.

STARTING MATERIALS

A. Preparation of Bicyclo[2.2.1]heptane-endo-2,3-dicarboxylic acid-5-endo-hydroxy-γ-lactone (II)

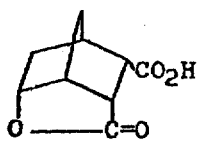

II

Five hundred grams (500 g.) of concentrated sulfuric acid was slowly added with vigorous stirring to a suspension of 164 g. of endo-cis-bicyclo[2.2.1]hept-5-ene-2,3-dicarboxylic anhydride in 500–600 ml. of water. The reaction was exothermic and the temperature rose to about 80°–90°C. during the addition of the sulfuric acid. Two liters of boiling water was added to the reaction solution and it was immediately filtered. As the filtrate was cooled, colorless platlets of the title product (II) crystallized. On completion of the crystallization, the crystals were collected by filtration and washed with cold water to produce 138 grams of air-dried crystals, m.p. 200°C.

B. General Method of Preparation of 5-endo-Hydroxy-N-[amino(lower)alkyl]bicyclo[2.2.1-]heptane-2,3-di-endocarboxylic Acid Imides (III)

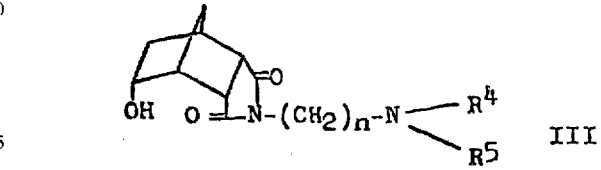

III

A mixture of 0.1 mole of lactone (II) from A supra and 50 ml. of thionyl chloride was refluxed on a water bath for 2 hours. The excess thionyl chloride was removed in vacuo and an oily residue (IIa) remained that was washed with n-hexane (or petroleum ether). The oily residue was dissolved in 50 ml. of anhydrous benzene. To this solution was added a solution of 0.12 moles of the appropriate amine, e.g., N,N-dimethylaminopropylamine, and 100 ml. of anhydrous benzene with stirring. The mixture was then refluxed for about 5 hours and concentrated in vacuo. The resultant brown syrupy substance (IIb) was refluxed for 5 hours in 300 ml of 50% water-ethanol containing 0.12 mole of potassium hydroxide. The solvents were removed in vacuo, saturated potassium carbonate solution added and the resultant solution extracted repeatedly using chloroform or 1:1 ethyl acetate-benzene. The collective organic extracts were washed with saturated sodium chloride solution and dried over anhydrous sodium sulfate. After filtration, the solution was concentrated in vacuo and the product was recovered by crystallization, chromatography and/or vacuum distillation wherein in formula III, $n$ is an integer of 2 to 4 inclusive, $R^4$ or $R^5$ is H, (lower)alkyl or when taken together with the nitrogen a radical of the formula

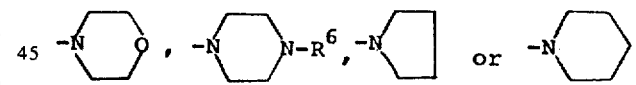

in which $R^6$ is (lower)alkyl.

C. Alternate Method of Preparation of 5-endo-Hydroxy-N-[amino(lower)alkyl]bicyclo[2.2.1-]heptane-2,3-di-endo-carboxylic Acid Imides (III)

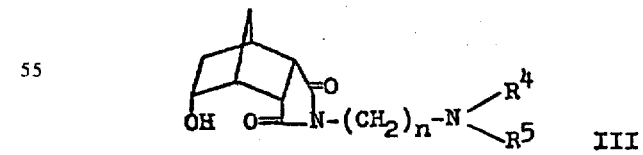

III

A mixture of 0.1 mole of lactone (II) from A supra and 30 ml. of PCl₃ was refluxed in a water bath for 2 hours. The excess PCl₃ was removed in vacuo and washed with n-hexane. The oily residue was dissolved in 50 ml. of chloroform or methylene chloride and a solution of 0.12 mole of an appropriate amine, e.g., N,N-dimethylaminopropylamine, dissolved in 100 ml. of anhydrous chloroform or methylene chloride was added with stirring and cooling. Stirring was continued for 2 hours, following which the mixture was warmed to room temperature following which the mixture was refluxed for about 15 minutes. The solution was washed with saturated potassium carbonate solution after cooling, separated, and the organic phase washed with saturated sodium chloride solution. The organic solution was dried over anhydrous sodium sulfate, filtered, and concentrated in vacuo. The material subsequently collected was the title product of formula III wherein n is an integer of 2 to 4 inclusive, $R^4$ or $R^5$ is H, (lower)alkyl or when taken together with the nitrogen a radical of the formula

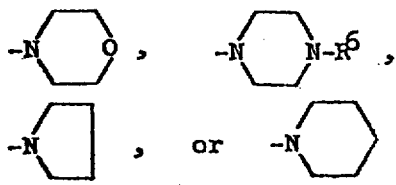

in which $R^6$ is (lower)alkyl.

D. Preparation of 5-endo-Hydroxy-N-(3-dimethylaminopropyl)-bicyclo[2.2.1]-heptane-2,3-di-endo-carboxylic Acid Imide (IIIa)

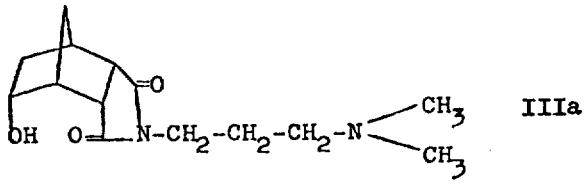

Substitution in the procedure B or C supra of an equimolar quantity of N,N-dimethylaminopropylamine for the "appropriate" amine used therein produced the title product as colorless plates when crystallized from ethanol-n-hexane; m.p. 148°C. (1 3/4 $H_2O$) or 154°C. (1/3 $H_2O$). Yield: 26–37%.

Anal. calc'd. for $C_{14}H_{22}O_3N_2 \cdot 1\cdot3/4\ H_2O$: C, 56.42; H, 8.79; N, 9.40.

Found: C, 56.70; H, 8.76; N, 9.11.

Anal. calc'd. for $C_{14}H_{22}O_3N_2 \cdot 1/3\ H_2O$: C, 61.76; H, 8.45; N, 10.29.

Found: C, 61.93; H, 8.76; N, 10.40.

E. Preparation of 5-endo-Hydroxy-N-(2-dimethylaminoethyl)bicyclo[2.2.1]heptane-2,3-di-endo-carboxylic Acid Imide (IIIb)

Substitution in the procedure B or C supra for the "appropriate" amine used therein of an equimolar quantity of N,N-dimethylaminoethylamine produced the title product. The free base was collected as colorless plates upon recrystallization from ethanol-n-hexane; m.p. 141.5°C. Yield: 50%

Anal. calc'd. for $C_{13}H_{20}O_3N_2 \cdot 1/3\ H_2O$: C, 60.46; H, 8.13; N, 10.85.

Found: C, 60.71; H, 8.04; N, 10.95.

F. Preparation of 5-endo-Hydroxy-N-(2-diethylaminoethyl)bicyclo[2.2.1]heptane-2,3-di-endo carboxylic Acid Imide Phenolphthalinate (IIIc)

Substitution in the procedure B supra for the "appropriate" amine used therein of an equivalent amount of N,N-diethylaminoethylamine produced the title product as yellow oil, b.p. 213°–220°C./5 mm. Hg. Yield: 37%. The product was further characterized as the phenolphthalinate salt, m.p. 137°–138.8°C.

Anal. calc'd. for $C_{35}H_{40}O_7N_2 \cdot 1½\ H_2O$: C, 67.04; H, 6.91; N, 4.48.

Found: C, 67.38; H, 7.41; N, 4.23

G. Preparation of 5-endo-Hydroxy-N-(3-diethylaminopropyl)bicyclo[2.2.1]heptane-2,3-di-endo-carboxylic Acid Imide Phenolphthalinate (IIId)

Substitution in the procedure B supra for the "appropriate" amine used therein of an equivalent amount of N,N-diethylaminopropylamine produced the title product as a yellow oil, b.p. 228°–230°C./6 mm. Hg. Yield: 34%. The product was further characterized as the phenolphthalinate salt, m.p. 155°–158°C.

Anal. calc'd. for $C_{36}H_{42}O_7N_2 \cdot 1½\ H_2O$: C, 67.39; H, 7.02; N, 4.36.

Found: C, 67.77; H, 6.79; N, 4.36.

H. Preparation of 5-endo-Hydroxy-N-(3-piperidinopropyl)bicyclo[2.2.1]heptane-2,3-di-endo-carboxylic Acid Imide (IIIe)

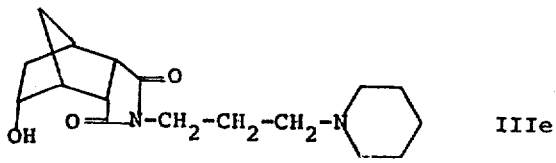

Substitution in the procedure B or C supra for the "appropriate" amine used therein of an equivalent amount of 3-piperidinopropylamine produced the title product as colorless plates upon recrystallization from isopropanol-n-hexane, m.p. 121.5°C. Yield: 50%.

Anal. calc'd. for $C_{17}H_{26}O_3N_2 \cdot ¼\ H_2O$: C, 65.70; H, 8.53; N, 9.01.

Found: C, 66.05; H, 9.03; N, 9.06.

I. Preparation of 5-endo-Hydroxy-N-(2-morpholinoethyl)bicyclo[2.2.1]heptane-2,3-di-endo-carboxylic Acid Imide Hydrochloride (IIIf)

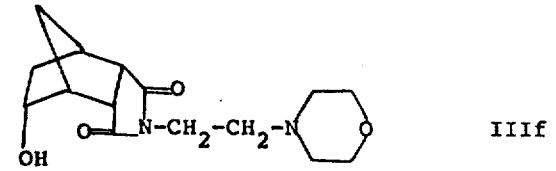

Substitution in the procedure B or C supra for the "appropriate" amine used therein of an equivalent amount of morpholinoethylamine produced the title compound which was collected as the hydrochloride. The hydrochloride salt was prepared by dissolving IIIf in a minimal amount of diethylether solution of dry HCl gas to the solution of IIIf with stirring and scratching. The resultant precipitate was collected by filtration. The hydrochloride was collected as colorless plates upon recrystallization from water-ethanol, m.p. 280°–282°C.

Yield: 30–34%.

Anal. calc'd. for $C_{15}H_{22}O_4N_2 \cdot HCl$: C, 54.43; H, 7.00; N, 8.46.

Found: C, 54.26; H, 7.56; N, 8.50.

J. Preparation of 5-endo-Hydroxy-N-(3-morpholinopropyl)bicyclo[2.2.1]heptane-2,3-di-endo-carboxylic Acid Imide (IIIg)

Substitution in the procedure B supra for the "appropriate" amine used therein of an equivalent amount of morpholinopropylamine produced the title product as a yellow oil, b.p. 260°–270°C./4 mm. Hg.; yield 50%. The product was further characterized as the methiodide salt; m.p. 233°C.

Anal. calc'd. for $C_{16}H_{24}O_4N_2 \cdot CH_3I$: N, 6.20.
Found: N, 6.28

K. General Method of Preparation of (±)-5-endo-benzoyloxy-N-[amino(lower)alkyl]bicyclo[2.2.1]heptane-2,3-di-endo-carboxylic Acid imides (L) (Starting Materials)

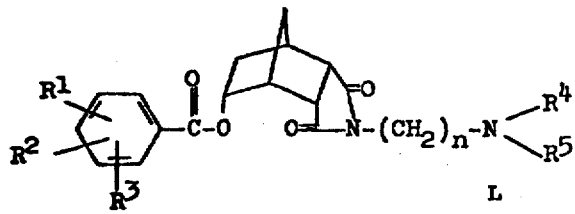

The 5-endo-Hydroxy-N-[amino(lower)alkyl]bicyclo[2.2.1]heptane-2,3-di-endo-carboxylic acid imide (III) (0.01 mole) obtained in B supra was added to 50 ml. of a 100:1 pyridine-piperidine solution of 0.012 mole of an appropriate benzoyl halide, e.g., benzoyl chloride, with stirring. The resultant mixture was allowed to stand overnight in a refrigerator or warmed in a water or oil bath. The mixture was poured into ice-water and saturated with sodium carbonate and then extracted with chloroform or 1:1 benzene-ethyl acetate. The combined organic extracts were washed with saturated sodium chloride solution and dried over anhydrous sodium sulfate. The solution was collected by filtration and concentrated in vacuo to yield the desired title product (L).

L. Preparation of (±)-5-endo-Benzoyloxy-N-(3-dimethylaminopropyl)-bicyclo[2.2.1]heptane-2,3-di-endo-carboxylic Acid Imide (Lb)

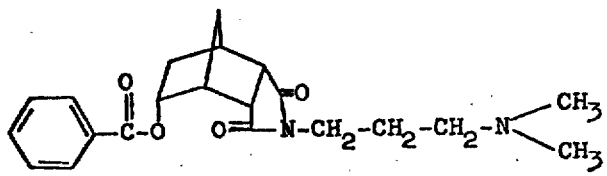

A. Substitution in the procedure of K supra of an equimolar quantity of benzoyl chloride for the "appropriate" benzoyl halide used therein and for the dicarboxylic acid imide III an equimolar quantity of IIIa produced the title product which was collected as the hydrochloride salt.

B. The free base was dissolved in near boiling ethanol (700 ml.) and 90 ml. of ethanol saturated with hydrogen chloride gas was added. The solution was cooled with ice to produce colorless plates of the hydrochloride salt of formula Lb; m.p. 239°C. with decomposition upon recrystallization from methanol-acetone. Yield-90%.

Anal. calc'd. for $C_{21}H_{27}O_4N_2Cl \cdot \frac{1}{3} H_2O$: C, 61.07; H, 6.83; N, 6.95.
Found: C, 60.63; H, 6.88; N, 7.33

M. Resolution of (±)-5-endo-Benzoyloxy-N-(3-dimethylaminopropyl)-bicyclo[2.2.1]heptane-2,3-di-endo-carboxylic Acid Imide Hydrochloride (Lb)

I. Preparation of the (−)-enantiomer.

A. (±)-5-endo-Benzoyloxy-N-(3-dimethylaminopropyl)bicyclo[2.2.1]heptane-2,3-di-endo-carboxylic Acid Imide (Lb).

A stirred mixture of the hydrochloride salt of Lb (10 g.) in water (150 ml.) and ether (200 ml.) was neutralized by the addition of sodium carbonate. The aqueous layer was re-extracted with ether (2 × 200 ml.). The combined ethereal extracts were washed with water, followed by water saturated with sodium chloride (3x) and dried (sodium sulfate). Removal of the ether left colorless crystals of the racemic base Lb (9.3 g.), m.p. 106°–107.5°.

B. (+)-10-Camphorsulfonic Acid Salt of (−)-5-endo-benzoyloxy-N-(3-dimethylaminopropyl)bicyclo[2.2.1-]heptane-2,3-di-endo-carboxylic Acid Imide.

A hot solution of (+)-10-camphorsulfonic acid (276.5 g., 1.19 mole) in ethanol (1.1.l) was added to a hot solution of the racemic base Lb (441.1 g., 1.19 mole) in ethanol (3.5.l)containing water (175 ml.). The solution was heated to near boiling and then rapidly cooled to 20°. The colorless crystalline material which formed during 3 hours standing at 20° was collected and washed with cold ethanol (600 ml.) to give 325.3 g. of the title product, m.p. 221°–226°. The salt was recrystallized from acetonitrile to give colorless needles (282.6 g.), m.p. 230°–233°. The ethanolic mother liquor was retained for isolation of the (+)-isomer.

C. (−)-5-endo-Benzoyloxy-N-(3-dimethylaminopropyl)bicyclo[2.2.1]heptane-2,3-di-endo-carboxylic Acid Imide [(−)-Lb].

The camphorsulfonic acid salt from step B (282.6 g.) was partitioned between a stirred mixture of ethyl acetate (3.5.l) and water (3.1) containing sodium carbonate (150 g.). The aqueous layer was reextracted with ethyl acetate (600 ml.). The combined ethyl acetate extracts were washed with water saturated with sodium chloride (3x), and dried (sodium sulfate). Removal of the ethyl acetate left the title product as colorless crystals (173.3 g.): m.p. 131.5°–132.5°; $[\alpha]_D^{25} -78.53°$ (c. 4.26, ethanol).

D. (−)-5-endo-Benzoyloxy-N-(3-dimethylaminopropyl)bicyclo[2.2.1]heptane-2,3-di-endo-carboxylic Acid Imide Hydrochloride (V).

To a near boiling solution of the (−)-isomer (173.3 g., 0.468 mole) from step C in 95% ethanol (3.5.1) was added 475 ml. of 95% ethanol, 0.988 molar in hydrogen chloride (0.468 mole of HCl). The solution was cooled in ice. The colorless crystals were collected, washed with cold 95% ethanol (600 ml.) and dried to give the title product (182.6 g.): m.p. 207°–209°; $[\alpha]_D^{25}$ −85.56° (c. 1.5, water). The m.p. and rotation were not significantly changed upon further recrystallization from 95% ethanol.

II. Preparation of the (+)-enantiomer.

A. (−)-Tartaric Acid Salt of (+)-5-endo-benzoyloxy-N-(3-dimethylaminopropyl)bicyclo[2.2.1]heptane-2,3-di-endo-carboxylic Acid Imide.

The ethanolic mother liquor from step I B. above was stored at 0° for 90 hours to give additional crystalline material (237.2 g.), m.p. 183°–186°. The filtrate was concentrated to give another crop of colorless crystals (119.9 g.), m.p. 168–177°. Both crops were combined and partitioned between ethyl acetate and aqueous sodium carbonate as described in I C. above to give a mixture of (+)- and (−)-isomers (221.4 g.), m.p. 125°–129°, greatly enriched in the (+)-enantiomer.

(−)-Tartaric acid (89.6 g., 0.596 mole) was added to a hot stirred solution of the (+)-enriched mixture (221.4 g., 0.596 mole) in ethanol (3.6.1.) containing water (40 ml.). The stirred mixture was heated to near boiling and then cooled to 25° during 4 hours. The colorless crystalline material was collected, washed with cold 95% ethanol (500 ml.) and dried to give the tartrate salt of the (+)-enantiomer (291.6 g.), m.p. 157°–161° (dec.). Recrystallization from acetonitrile gave 247.2 g. of the purified tartrate salt, m.p. 162°–164° (dec.).

B. (+)-5-endo-Benzoyloxy-N-(3-dimethylamino-propyl)bicyclo[2.2.1]heptane-2,3-di-endo-carboxylic Acid Imide [(+)-Lb].

The tartrate salt from step A (247.2 g.) was decomposed with aqueous sodium carbonate and the liberated (+)-enantiomer extracted into ethyl acetate as described in I.C. Removal of the ethyl acetate left the (+)-isomer (171.6 g.), as colorless crystals: m.p. 131°–133.5°; $[\alpha]_D^{25}$ + 77.74° (c. 1.89, ethanol).

C. (+)-5-endo-Benzoyloxy-N-(3-dimethyl-amino-propyl)bicyclo[2.2.1]heptane-2,3-di-endo-carboxylic Acid Imide Hydrochloride (VI).

The (+)-enantiomer (171.6 g.) from step B was treated with an equivalent of ethanolic hydrogen chloride as described for the (−)enantiomer in I D. to give colorless crystals of the (+)-enantiomer HCl, (188.2 g.): m.p. 207°–209°; $[\alpha]_D^{25}$ +85.88° (c. 1.36, water).

N. Preparation of 5-endo-Hydroxy-N-(4-dimethylaminobutyl)-bicyclo[2.2.1]heptane-2,3-di-endo-carboxylic acid imide (IIIk)

To a stirred mixture of 5-endo-hydroxy-bicyclo[2.2.1]heptane-2,3-di-endo-carboxylic acid-γ-lactone (II) (15.2 g., 0.144 moles) in 100 ml of dry $CH_2Cl_2$ was added thionyl chloride (25 ml) and DMF (3 drops). The mixture was stirred and refluxed for 3 hrs. The reaction solution was then cooled to 23°C., and the solvent stripped under reduced pressure. The remaining yellow oil was taken up in 50 ml. of benzene and stripped to dryness under reduced pressure to yield a pale yellow solid. The solid was dissolved in 100 ml of $CH_2Cl_2$ and 4-dimethylaminobutylamine (20 g., 0.173 moles) in 50 ml of $CH_2Cl_2$ was added dropwise. After the addition was complete, the reaction mixture was stirred at 23°C. for 2½ hours. The reaction mixture was then treated with saturated $K_2CO_3$ solution and the phases separated. The aqueous phase was extracted 2 × 125 ml of $CH_2Cl_2$ and all $CH_2Cl_2$ phases were combined, washed with saturated NaCl solution, dried over $Na_2SO_4$, filtered, and stripped under reduced pressure. The resulting pale yellow oil was treated with boiling EtOAc and the EtOAc solution decanted and stripped under reduced pressure to yield a pale yellow solid. This solid was recrystallized from EtOAc to give IIIk as light yellow crystals (13.3 g., 33.3%, mp 108°–109°C).

Anal. calc'd. for $C_{15}H_{24}N_2O_3$: C, 64.26; H, 8.63; N, 9.99.

Found: C, 64.21; H, 8.46; N, 10.02 (corrected for 1.61% $H_2O$).

DESCRIPTION OF THE PREFERRED EMBODIMENTS

EXAMPLE 1

General Method of Preparation of 5-endo-(3-indolecarbonyloxy)-N-[amino(lower)alkyl]bicy-

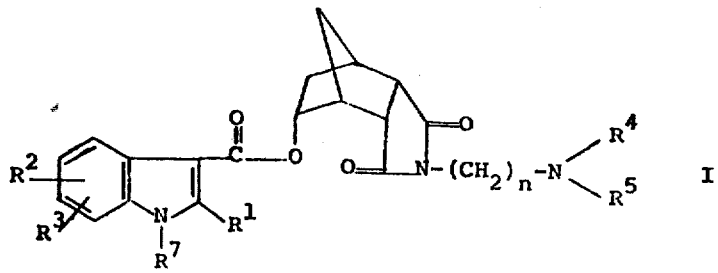

clo[2.2.1]heptane-2,3-di-endo-carboxylic Acid Imides (I).

(±)-5-endo-Hydroxy-N[amino(lower)alkyl]bicyclo[2.2.1]heptane-2,3-di-end-carboxylic acid imide (III) (0.01 mole) was added to a dry solution of appropriately substituted indole-3-carbonyl halide (0.011 mole), e.g., indole-3-carbonyl chloride, in methylene chloride containing approximately 1 ml. of pyridine, with stirring. The resultant mixture was allowed to stand overnight in a refrigerator or warmed in a water or oil bath. The mixture was poured into ice-water and saturated with sodium carbonate and then extracted with chloroform or 1:1 benzene-ethyl acetate. The combined organic extracts were washed with saturated sodium chloride solution and dried over anhydrous sodium sulfate. The solution was collected by filtration and concentrated in vacuo to yield the desired title product (I).

EXAMPLE 2

5-endo-(3-Indolecarbonyloxy)-N-(3-dimethylamino-propyl)-bicyclo[2.2.1]heptane-2,3-di-endo-carboxylic acid imide, hydrochloride [(±) -BL-4712A; (±)-la].

To a suspension of indole-3-carboxylic acid (6.44 g., 0.04 mole) in 100 ml. of dry $Et_2O$ was added 306 ml. (0.05 mole) of thionyl chloride and the mixture was stirred under anhydrous conditions for 2 hrs. The solvent and excess thionyl chloride were removed by evaporation under reduced pressure at 25°–30°, affording an oil. The oil was treated with an additional volume of dry $Et_2O$ which was then removed as above, yielding a solid whose infrared spectrum was consistent for the desired indole-3-carbonyl chloride. This acid chloride (7.16 g., 0.04 mole) was dissolved in 100 ml. of dry $CH_2Cl_2$ containing 13 drops of dry pyridine. The alcohol (±) IIIa (5.32 g., 0.02 mole) was added and the mixture was stirred at 25°. Within 5 mins., a heavy solid precipitated and a further 20 ml. of dry pyridine was added to achieve solution. After refluxing the mixture for about 10 mins., the product precipitated from solution. Cooling and filtration gave 7.6 g. (86%) of crude BL-4712A and the purified material was obtained upon recrystallization from 20:1 EtOH/MeOH; m.p. 256° C.

Anal. Calc'd. for $C_{23}H_{27}N_3O_4 \cdot HCl$: .HCl: C, 62.09; H, 6.12; N, 9.44; Cl, 7.97.

Found: C, 62.27; H, 6.19; N, 9.39; Cl, 7.95.

EXAMPLE 3

Preparation of 5-endo-(2-methyl-3-indolecarbonyloxy)-N-(3-dimethylaminopropyl)-bicyclo[2.2.1]heptane-2,3-di-endo-carboxylic acid imide hydrochloride [(±)-Ib].

Substitution in the procedure of example 2 for the indole-3-carbonyl chloride used therein of an equimolar quantity of 2-methylindole-3-carbonyl chloride produces the title product (±)-Ia.

EXAMPLE 4

Preparation of 5-endo-(2-bromo-3-indolecarbonyloxy)-N-(3-dimethylaminopropyl)-bicyclo[2.2.1]heptane-2,3-di-endo-carboxylic acid imide hydrochloride [(±)-Ic].

Substitution in the procedure of example 2 for the indole-3-carbonyl chloride used therein of an equimolar quantity of 2-bromoindole-3-carbonyl chloride produces the title product (±)-Ic.

EXAMPLE 5

Preparation of 5-endo-(3-indolecarbonyloxy)-N-(3-morpholinopropyl)bicyclo[2.2.1]heptane-2,3-di-endo-carboxylic acid Imide [(±)-Ig].

Substitution in the procedure of example 1 for the dicarboxylic acid imide III used therein of an equimolar quantity of IIIg produces the title product (±)-Ig.

EXAMPLE 6

Preparation of 5-endo-(3-indolecarbonyloxy)-N-(2-dimethylaminoethyl)bicyclo[2.2.1]heptane-2,3-di-endo-carboxylic Acid Imide [(±) (Ih)].

Indole-3-carbonyl acid (4.52 g., 28 mmoles) was converted to the acid chloride in the usual manner. The acid chloride was redissolved in dry $CH_2Cl_2$ (100 ml) and the alcohol III (4.8 g., 19 mmoles) and dry pyridine (1 ml) were then added with stirring. After refluxing the mixture for 70 mins., the product precipitated as a white solid, (6.7 g., 81.6%). An analytical sample was obtained by recrystallization from 2:1 isopropyl alcohol/MeOH; mp 259°–261°(d).

Anal. calc'd. for $C_{22}H_{25}N_3O_4 \cdot HCl$: C, 61.18; H, 6.07; N, 9.73.

Found: C, 61.53; H, 6.10; N, 9.85.

EXAMPLE 7

Preparation of 5-endo-(3-indolecarbonyloxy)-N-(3-piperidinopropyl)bicyclo[2.2.1]heptane-2,3-di-endo-carboxylic Acid Imide (Ii).

Substitution in the procedure of example 1 for the dicarboxylic acid imide III used therein of an equimolar quantity of IIIe produced the title compound.

EXAMPLE 8

Preparation of 5-endo-(3-indolecarbonyloxy)-N-(3-methylaminopropyl)bicyclo[2.2.1]heptane-2,3-di-endo-carboxylic Acid Imide Hydrochloride (Ij).

A. 5-endo-[1-(2,2,2-trichloroethoxycarbonyl)-3-indolecarbonyloxy]-N-[3-(2,2,2-trichloroethoxycarbonyl)-3-methylaminopropyl]bicyclo[2.2.1]heptane-2,3-di-endo-carboxylic Acid Imide.

To a solution of compound Ia (8.8 g., 21.5 mmoles) in 100 ml of dry pyridine was added, portionwise and with stirring over 15 mins., trichloroethyl chloroformate (9.53 g., 45 mmoles). Stirring at 20° C. was continued for 20 mins., followed by heating at 60°–65° in an oil bath for 75 mins. The clear amber solution was then cooled and stripped of solvent under reduced pressure at 45°. The residue was dissolved in $CH_2Cl_2$ (300 ml) and washed successively with $H_2O$, cold dil. HCl, $H_2O$, 5% $Na_2CO_3$ solution and brine. Drying ($MgSO_4$) and solvent removal gave a mixture of s-endo-[1-(2,2,2-trichloroethoxycarbonyl)-3-indolecarbonyloxy]-N-(3-dimethyl(aminopropyl)bicyclo[2.2.1-]heptane-2,3-di-endo-carboxylic acid imide (7a) and 5-endo-[1-(2,2,2-trichloroethoxycarbonyl)-3-indolecarbonyloxy]-N-[3-(2,2,2-trichloroethoxycarbonyl)-3-methylaminopropyl]-bicyclo[2.2.1]heptane-2,3-di-endo-carboxylic acid imide (7b) as an amber gum (16 g.). Trituration with $Et_2O$ gave a white solid which was then recrystallized from $EtOAc/Et_2O$ (some insolubles were removed by filtration), to give essentially pure 7b (5.6 g., 35%, mp 178°–182° (d)).

7b (1.95 g., 2.61 mmoles) was suspended in 90% HoAc (100 ml) and 7 g. of zinc dust was added portionwise with stirring over 1 min. (slightly exothermic). After stirring at 20° for 21 hrs., the excess zinc and salts were removed by filtration, washing the cake with 30 ml of 90% HOAc. The filtrate was stripped at ~40° and the remaining gum was treated with saturated $NaHCO_3$ solution (frothing) and then 1N NaOH solution until distinctly basic. Extraction with two portions of EtOAc was followed by washing of the organics with $H_2O$ and brine. Drying ($MgSO_4$) and stripping afforded a gum (0.833 g.), which was dissolved in 2:1 abs $EtOH/Et_2O$ and treated with HCl gas. Solvent removal and trituration of the resultant gum with hot 3:1 EtOAc/abs EtOH gave the crude hydrochloride salt (0.622 g., 55.4% mp 243°–247° (d)). Boiling in 3:1 $CH_3CN$/abs EtOH and dilution with $Et_2O$ gave pure IJ in two crops (mp 246°–249°(d)).

Anal. calc'd. for $C_{22}H_{25}N_3O_4 \cdot HCl$: .HCl: C, 61.18; H, 6.07; N, 9.73.

Found: C, 60.98; H, 6.03; N, 10.06.

EXAMPLE 9

Preparation of 5-endo-(3-indolecarbonyloxy)-N-(3-aminopropyl)bicyclo[2.2.1]heptane-2,3-di-endo-carboxylic acid imide (Ik).

A. 5-endo-Hydroxy-bicyclo[2.2.1]heptane-endo-2[N-(2-cyanoethyl)]carboxamide-endo-3-carboxylic acid γ-lactone (XX).

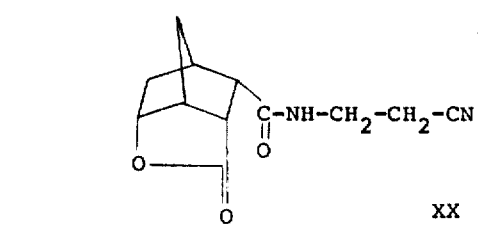

XX

A mixture of lactone-acid II (18.2 g; 0.1 mole), 150 ml. SOCl$_2$ and 250 ml CH$_2$Cl$_2$ containing 4 drops of DMF (dimethylformamide) was refluxed (60°C.) for 3 hours. After evaporating to dryness, benzene was added and removed under reduced pressure. After dissolving the acid chloride in 350 ml CH$_2$Cl$_2$, there was added dropwise with vigorous stirring a solution of 3-aminopropionitrile (15.3 g; 0.21 mole) in 150 ml CH$_2$Cl$_2$. The resulting reaction mixture was refluxed for 2 hours. After cooling and filtering the insoluble materials, the filtrate was evaporated to dryness. The residue, so obtained, was slurried with a small amount of CH$_3$CN to which ether was carefully added. In this way, the crystalline product was obtained in 85.5% yield with mp 129°–135°C. A sample on recrystallization from CH$_3$CN gave analytically pure material, mp 145°–147° C.

Anal. calc'd. for C$_{12}$H$_{14}$N$_2$O$_3$: C, 61.52; H, 6.02; N, 11.96.

Found: C, 61.54; H, 6.28; N, 11.96.

B. 5-endo-(3-indolecarbonyloxy)-N-(2-cyanoethyl)-bicyclo[2.2.1]heptane-endo-2,3-dicarboxylic acid imide (XI).

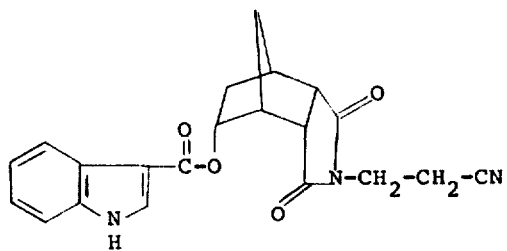

XI

To a mixture of indole-3-carboxylic acid (9.4 g 0.058 moles) in dry Et$_2$O (200 ml) was added thionyl chloride (15 ml) and DMF (3 drops). After 3 hrs. of stirring at 23°C., the reaction mixture was filtered and the filtrate evaporated under reduced pressure to yield a dark solid. The solid was taken up in dry CH$_2$Cl$_2$ (150 ml) and pyridine (2 ml) and 5-endo-hydroxy-bicyclo[2.2.1-]heptane-endo-2-[N-(2-cyanoethyl)]carboxamide-endo-3-carboxylic acid γ-lactone XX (9.0 g. 0.038 moles) was added. The reaction mixture was refluxed for 15 hours and filtered. The filtrate was evaporated under reduced pressure and the resulting residue was crystallized from CH$_3$CN to yield the desired product XXI (6.8 g., 48%, mp 230°–231°).

Anal. calc'd. for C$_{22}$H$_{19}$N$_3$O$_4$: C, 66.83; H, 5.07; N, 11.13.

Found: C, 67.00; H, 5.01; N, 10.78.

C. 5-endo-(3-indolecarbonyloxy)-N-(3-aminopropyl)bicyclo[2.2.1]heptane-endo-2,3-dicarboxylic acid imide imide hydrochloride (Ik).

The nitrile XXI (1.0 g. 0.0027 moles) and 1 gm of 30% Palladium catalyst on diatomaceous earth in 175 ml of 95% EtOH/5% Hydrochloric acid were shaken in a Parr Hydrogenation apparatus under a Hydrogen atmosphere of 50 lbs. After 60 hours of shaking, hydrogen pressure in the bottle had dropped 19 lbs. At this time, the reaction mixture was depressurized and filtered. The filtrate was evaporated to dryness under reduced pressure, treated with 5% Na$_2$CO$_3$, and evaporated to dryness. The residue was washed with four 150 ml portions of CH$_2$Cl$_2$ and the CH$_2$Cl$_2$ portions combined, dried over Na$_2$SO$_4$, filtered and evaporated to dryness. The residue was recrystallized from CH$_2$Cl$_2$/Skelly B to yield 0.84 g of free base. This was taken up in EtOH and poured into Et$_2$O saturated with HCl gas. A gel-like mixture resulted. The gel was evaporated to dryness and the residue boiled in EtOH with charcoal, filtered, and stripped under reduced pressure. At this stage, the material was an ethanol solvate. To remove the solvate, the material was boiled in the following series of solvents: EtOAc, CH$_2$Cl$_2$ and Skelly C. The elemental analysis, mass spectrum and 100 MHz nmr of the material at this stage were consistent for the desired primary amine analogue Ik. The compound was assayed by 100 MHz nmr to be a 0.12 molar CH$_2$Cl$_2$ solvate. When boiled with EtOAc, the compound exists as a 0.18 molar EtOAc solvate. Heat and vacuum could not remove these solvates, (0.84 g, 84%, mp 185°–190°).

Anal. calc'd. for C$_{21}$H$_{23}$N$_3$O$_4$·°HCl: C, 60.36; H, 5.79; N, 10.06; Cl, 8.49.

Found: C, 59.61; H, 5.86; N, 10.02; Cl, 9.03. (Corrected for 1.24% H$_2$O and 1.67% CH$_2$Cl$_2$).

EXAMPLE 10

Preparation of 5-endo-(1-methylindolecarbonyloxy)-N-(3-dimethylaminopropyl)bicyclo[2.2.1]heptane-2,3-di-endo-carboxylic acid imide [(±)-Iv].

Substitution in the procedure of example 6 for the 3-indolecarbonyl chloride used therein of an equimolar quantity of 1-methylindole-3-carbonyl chloride produces the title product (±)-Iv.

EXAMPLE 11

Preparation of 5-endo-(4-methyl-3-indolecarbonyloxy)-N-(3-dimethylaminopropyl)bicyclo[2.2.1]heptane-2,3-di-endo-carboxylic acid imide [(±)-Iw].

Substitution in the procedure of example 6 for the 3-indolecarbonyl chloride used therein of an equimolar quantity of 4-methyl-3-indolecarbonyl chloride produces compound (±)-Iw.

Example 12

Preparation of 5-endo-(4-methoxy-3-indolecarbonyloxy)-N-(3-dimethylaminopropyl)bicyclo[2.2.1]heptane-2,3-di-endo-carboxylic acid imide [(±)-Ix].

Substitution in the procedure of example 6 for the 3-indolecarbonyl chloride used therein of an equimolar quantity of 4-methoxy-3-indolecarbonyl chloride produces the compound (±)-Ix.

Example 13

Preparation of 5-endo-(4-trifluoromethyl-3-indolecarbonyloxy)-N-(3-dimethylaminopropyl)bicyclo[2.2.1]heptane-2,3-di-endo-carboxylic acid imide [(±)-Iy].

Substitution in the procedure of example 2 for the 3-indolecarboxylic acid used therein of an equimolar quantity of 4-trifluoromethyl-3-indolecarbonyloxy produces compound (±)-Iy.

Example 14

Preparation of 5-endo-(5-hydroxy-3-indolecarbonyloxy)-N-(3-dimethylaminopropyl)bicyclo[2.2.1]heptane-2,3-di-endo-carboxylic acid imide [(±)-Iq].

Substitution in the procedure of example 2 for the 3-indolecarbonyl chloride used therein of an equimolar quantity of 5-hydroxy-3-indolecarbonyl chloride produces compound (±)-Iq.

Example 15

Preparation of 5-endo-(5-methoxy-3-indolecarbonyloxy)-N-(3-dimethylaminopropyl)bicyclo[2.2.1]heptane-2,3-di-endo-carboxylic acid imide [(±)-Ir].

Substitution in the procedure of example 2 for the 3-indolecarbonyl chloride used therein of an equimolar quantity of 5-methoxy-3-indolecarbonyl chloride produces compound (±)-Ir.

EXAMPLE 16

Preparation of 5-endo-(5-methyl-3-indolecarbonyloxy)-N-(3-dimethylaminopropyl)bicyclo[2.2.1]heptane-2,3-di-endo-carboxylic acid imide [(±)-Is].

Substitution in the procedure of example 2 for the 3-indolecarbonyl chloride used therein of an equimolar quantity of 5-methyl-3-indolecarbonyl chloride produces the compound (±)-Is.

Example 17

Preparation of 5endo-(2,4-dimethyl-3-indolecarbonyloxy)-N-(3-dimethylaminopropyl)bicyclo[2.2.1]heptane-2,3-di-endo-carboxylic acid imide [(±)-It].

Substitution in the procedure of example 2 for the 3-indolecarbonyl chloride used therein of an equimolar quantity of 2,4-dimethyl-3-indolecarbonyl chloride produces the compound (±)-It.

Example 18

Preparation of 5-endo-(6-chloro-5-methoxy-2-methyl-3-indolecarbonyloxy)-N-(3-dimethylaminopropyl)-bicyclo[2.2.1]heptane-2,3-di-endo-carboxylic acid imide [(±)-Iu].

Substitution in the procedure of example 2 for the 3-indolecarbonyl chloride used therein of an equimolar quantity of 6-chloro-5-methoxy-2-methyl-3-indolecarbonyl chloride produces the title compound [(±)-Iu].

Example 19

(±)-5-Endo-(3-Indolecarbonyloxy)-N-(3-dimethylaminopropyl)bicyclo[2.2.1]heptane-2,3-di-endo-carboxylic acid Imide, Hydrochloride [BL-4764A, (±)-Ia].

A. (±)-5-Endo-Hydroxy-N-(3-dimethylaminopropyl bicyclo[2.2.1]heptane-2,3-di-endo-carboxylic acid Imide [(±)-IIIa].

(±)-5-Endo-benzoyloxy-N-(3-dimethylaminopropyl)bicyclo[2.2.1]heptane-2,3-di-endo-carboxylic acid amide hydrochloride (3.65 g. 0.0086 mole) [(±)-Lb] was suspended in 18.8 ml of 1.0N NaOH and heated to reflux with stirring for 45 minutes in an oil bath at 120°–125° C. The solution was then cooled, filtered and evaporated under reduced pressure to yield a white solid. The solid was then triturated with three 80 ml aliquots of hot EtOAc. The aliquots were combined and evaporated to yield an oil which solidified upon cooling. The solid was then resuspended in 100 ml cyclohexane and 15 ml EtOAc and heated to a reflux. Filtration of the hot solution and cooling to 20° C yielded a crystalline solid (1.53 g; 67% mp 121°–122° C determined to be (±)-IIIa.

B. (±)-5-Endo-(3-Indolecarbonyloxy)-N-(3-dimethylaminopropyl)bicyclo[2.2.1]heptane-2,3-di-endocarboxylic acid imide, hydrochloride [(±)-Ia, BL-4764A].

To a stirred mixture of indole-3-carboxylic acid (2.6 g, 0.015 mole) in $Et_2O$ (40 ml) was added 3.0 ml of thionyl chloride and 1 drop of anhydrous dimethyl formamide (DMF). After stirring at 23° for 3 hrs., the mixture was filtered and the filtrate was stripped of excess reagent and solvent to yield the crude acid chloride (2.6 g) as a dark semi solid syrup. The acid chloride was taken up in 40 ml of dry $CH_2Cl_2$, 5 drops of pyridine were then added, followed by the (±)-IIIa alcohol (2.0 g, 0.0075 mole). The mixture was stirred at reflux for 2 hours under anhydrous conditions and then stripped of solvents under reduced pressure. The dark residue was chromatographed through a column of basic alumina (100 g), the product being eluted with 45% $CHCl_3$/45% $Et_2O$/10% MeOH. The fractions containing the product were stripped of solvent, and the resultant yellowbrown oil was redissolved in 75% $Et_2O$-25% EtOH and treated with HCl gas. Solvent removal, recrystallization of the crude solid from EtOH, and drying at 78° over $P_2O_5$ under high vacuum gave the pure hydrochloride salt. (0.921 g; 27.6% yield; mp 193°–195°).

Anal. Calc'd. for $C_{23}H_{27}N_3O_4 \cdot HCl$: C, 61.95; H, 6.33; N, 9.42; Cl, 7.95.

Found [Corrected for 1.65% $H_2O$): C, 62.45; H, 6.41; N, 9.74; Cl, 8.13. $[\alpha]_{589}^{23°} = +57.8$ (C=0.069 g; $H_2O$).

Example 20

(−)-5-Endo-(3-Indolecarbonyloxy)-N-(3-dimethylaminopropyl)bicyclo[2.2.1]heptane-2,3-di-endocarboxylic acid imide, hydrochloride [BL-4763A, (−)-Ia].

A. (−)-5-Endo-Hydroxy-N-(3-dimethylaminopropyl)bicyclo[2.2.1]heptane-2,3-di-endo-carboxylic acid imide [(−)-IIIb].

Substitution in the procedure of example 19A for the compound (±)-Lb used therein of an equimolar quantity of (−)-Lb produced compound (−)-IIIa; m.p. 119°–120°C.

B. (−)-5-Endo-(3-Indolecarbonyloxy-N-(3-dimethylaminopropyl)bicyclo[2.2.1]heptane-2,3-diendocarboxylic acid imide, hydrochloride (BL-4763A).

Indole-3-carboxylic acid (2.6 g, 0.015 mole) was converted to the crude acid chloride as described above for BL-4764A. Treatment with the (−)-IIIa alcohol (2.0 g; 0.0075 mole) in $CH_2Cl_2$/pyridine as described for BL-4764A gave the crude product. Chromatography on a column of basic alumina (100 g) gave the purified free base upon elution with 33% $CHCl_3$/12% $Et_2O$/55% MeOH. The fractions containing the product were stripped of solvent, and the residual crude oil was taken up in 75% Et₂O-25% EtOH and treated with HCl gas. Solvent removal gave the hydrochloride as a crude brown solid. Two recrystallizations from EtOH, followed by trituration with hot EtOAc and drying at 78° over P₂O₅ under high vacuum gave the product (1.47 g; 44% yield; m.p. 172°–174°).

Anal. calc'd. for $C_{23}H_{27}N_3O_4$.HCl: C, 61.95, H, 6.33; N, 9.42; Cl, 7.95.

Found (corrected for 5.02% H₂O): C, 62.01; H, 6.07; N, 9.52; Cl, 8.22. $[\alpha]_{589}^{23°} = -58.2$ (C=0.052; H₂O)

Example 21

5-endo-(Indole-3-carbonyloxy)-N-(2-dimethylaminopropyl)bicyclo[2.2.1]heptane-2,3-di-endo carboxylic acid imide hydrochloride, EtOH solvate (22)

The lactone acid II (8.0 g., 44 mmoles), SOCl₂ (12 ml) and dry DMF 20 drops) were suspended in dry CH₂Cl₂ (200 ml) and the mixture was stirred at reflux for 1.5 hr. The usual workup afforded the crude acid chloride which was redissolved in dry CH₂Cl₂ (150 ml). A solution of 2-dimethylamino-n-propylamine (6.74 g., 66 mmoles) in 50 ml of dry CH₂Cl₂ was then added dropwise with stirring over 10 mins. The mixture was refluxed for 3 hrs., stirred at 18° for 16 hrs. and then worked up by washing of the CH₂Cl₂ solution with 5% Na₂CO₃ solution and saturated brine, followed by drying (MgSO₄) and solvent removal.

The 5-endo-hydroxy-N-(2-dimethylaminopropyl)-bicyclo[2.2.1]heptane-2,3-di-endo-carboxylic acid imide (III) was obtained as a crude amber oil. A solid impurity was removed by trituration with EtOAc-Skellysolve B and filtering off the impurity. The purified oil IIm (11.4 g., 42.8 mmoles, 97.4%) was added to indole-3-carbonyl chloride (from 10.0 g., 62 mmoles of indole-3-COOH in the usual manner) in dry CH₂Cl₂ (200 ml) containing dry pyridine (2 ml) as outlined in Example 6. The product Im separated from the reaction mixture after 16 hrs. of heating at reflux, (6.71 g., 35.2%). Recrystallization from abs. EtOH/Et₂O gave the purified product as an EtOH solvate; mp 266°–270° (d). This solvate could not be removed at 110°/0.05 mm or by trituration with other solvents such as EtOAc at the boiling point.

Anal. Calc'd. for $C_{23}H_{27}N_3O_4$.HCl. EtOH: C, 61.03; H, 6.97; N, 8.54.

Found: C, 61.48; H, 6.63; N, 8.76.

EXAMPLE 22

5-endo-(Indole-3-carbonyloxy)-N-(4-dimethylaminobutyl)bicyclo[2.2.1]heptane-2,3-di-endo carboxylic acid imide hydrochloride (In).

To a stirred mixture of indole-3-carboxylic acid (5.0 g., 0.031 moles) in dry Et₂O (100 ml) was added thionyl chloride (7.5 ml) and DMF (2 drops). The mixture was stirred at 23°C. for 1 hr., followed by filtration and stripping of the filtrate under reduced pressure. The remaining solid acid chloride (5.3 g., 0.03 moles) was dissolved in CH₂Cl₂ (130 ml) and pyridine (1 ml), and the 5-endo alcohol IIIk (5.8 g., 0.021 moles) was added. The reaction mixture was refluxed for 1 hr. and then stripped of solvent under reduced pressure. The residue was then treated with 5% aqueous potassium carbonate solution (200 ml) and EtOAc (200 ml). The phases were separated and the aqueous phase was extracted with 2 × 100 ml EtOAc. The combined EtOAc portions were then dried over MgSO₄, filtered, and evaporated under reduced pressure to yield a dark brown residue. The residue was taken up in 100 ml of 1:1 EtOH:Et₂O and treated with HCl gas. This solution was stripped under reduced pressure to yield a brown solid. This solid was taken up in EtOH/EtOAc, treated with charcoal and recrystallized (3.7 g., 38% mp 217°–218°C).

Anal. Calc'd. for $C_{24}H_{29}N_3O_4$.HCl: C, 62.67; H, 6.57; N, 9.14; Cl, 7.71.

(Corrected for 0.6% H₂O) Found: C, 62.21; H, 6.86; N, 8.85; Cl, 7.88.

EXAMPLE 23

5-endo-(Indole-3-carbonyloxy)-N-(3-isopropylaminopropy)bicyclo[2.2.1]heptane-2,3-di-endo carboxylic acid imide hydrochloride (Io).

a. 5-endo-Hydroxy-N-(3-isopropylaminopropyl)-bicyclo[2.2.1]heptane-2,3-di-endo carboxylic acid imide hydrochloride (IIIm)

The lactone acid II (16.0 g., 88 mmoles) was converted to the lactone acid chloride in the usual manner. The acid chloride was dissolved in dry CH₂Cl₂ (120 ml) and added dropwise with stirring over 10 mins. to a cooled (ice-H₂O bath) solution of N-isopropyl-1,3-propanediamine (12.08 g., 0.104 mole) in dry CH₂Cl₂ (300 ml). The mixture was refluxed for 2 hrs., maintained at 18° for a further 16.5 hrs., and then filtered to remove a small quantity of solid amine salt. The filtrate was stripped of solvent under reduced pressure to give a syrup. The syrup was dissolved in hot EtOAc containing sufficient abs. EtOH to achieve solution. Cooling to 4° afforded the product IIIn (20.15 g., 72.3%) in two crops (mp 164°–167°). Recrystallization from EtOAc-/abs EtOH gave analytical material; mp 168°–172°.

Anal. Calc'd. for $C_{15}H_{24}N_2O_3$.HCl: C, 56.87; H, 7.95; N, 8.76.

Found: C, 56.63; H, 8.14; N, 8.76.

b. 5-endo-Hydroxy-N-(N'-benzyloxycarbonyl-3-isopropylaminopropyl)bicyclo[2.2.1]heptane-2,3-di-endo carboxylic acid imide XX The isopropylamino alcohol IIIm (3.17 g., 10 mmoles) was dissolved in 125 ml H₂O and anhydrous Na₂CO₃ (3.18 g., 30 mmoles) was added with mechanical stirring. After cooling the mixture to −5° (ice-H₂O), carbobenzyloxy chloride (2.05 g., 12 mmoles) was added dropwise over 1–2 mins. A white solid began to separate from the mixture within 5 mins. Stirring at −5° was continued for 15 mins., and then at 20° for 17 hours. The white precipitate was filtered, washed with H₂O, Skelly solve B and air dried (3.09 g., 74.6%). Pure XX was obtained by recrystallization from EtOAc-Skelly solve B; mp 96.5°–100°.

Anal. calc'd. for $C_{23}H_{30}N_2O_5$: C, 66.64; H, 7.30; N, 6.76.

Found: C, 66.71; H, 7.42; N, 6.74.

c. 5-endo-(Indole-3-carbonyloxy)-N-(3-isopropylaminopropyl)bicyclo[2.2.1]heptane-2,3-diendo carboxylic acid imide hydrochloride (Io) (BL-5006A).

Indole-3-carboxylic acid (0.644 g., 4 mmoles) and carbonylidiimidazole (1.3 g., 8 mmoles) were refluxed in dry THF (60 ml) for 3 hrs. Concentration of the reaction mixture to a volume of approximately 10 ml and cooling at 5° gave indole-3-imidazolide (25, 0.485 g., 57.4%) as a white solid after filtration and washing with Et₂O. The imidazolide 25 (0.37 g., 1.75 mmoles) and the carbobenzyloxy derivative XX (0.472 g., 1.14 mmoles) were then heated in dry tetrachloroethane (75 ml) at 120° for 2.75 hrs. The solvent was removed under reduced pressure and the residual oil was partitioned between EtOAc and H₂O. After separation of the layers, the aqueous layer was extracted with a second portion of EtOAc. The combined organics were washed with H₂O and brine, then dried (MgSO₄) and stripped of solvent to give a semisolid gum. Trituration with Et₂O left a white solid undissolved which was removed by filtration (imidazolide). The filtrate was stripped of solvent, redissolved in 6 ml of 1:1 Et₂O-CHCl₃ and filtered through a 3″ layer of basic alumina in a sintered glass funnel, eluting with 400 ml of 1:1 Et₂O-CHCl₃ + 2% MeOH solution. Stripping of the filtrate gave purified 5-endo(indole-3-carbonyloxy)-N-(N'-benzyloxycarbonyl-3-isopropylaminopropyl)bicyclo[2.2.1]heptane-2,3-di-endo-carboxylic acid imide as an oil (0.585 g). Hydrogenolysis of this intermediate was carried out in a Parr shaker at 48 psi in 100 ml of absolute EtOH, using 0.4 g of 30% Palladium on Celite as catalyst. The H₂ uptake was 7.5 lbs. over 1.25 hr. Removal of the catalyst and solvent afforded a white froth (0.448 g) which was redissolved in 1:1 abs EtOH-Et₂O and treated with HCl gas. Solvent removal and treatment of the residue with boiling 10:1 EtOAc-EtOH gave Io as a white solid (0.219 g). Initial elemental analysis indicated that the material had coordinated with a metal at some stage. It was, therefore, slurried in EtOAc and converted back to the free base by treatment with 3% Na₂CO₃ solution. The organic layer was then washed with 3 portions of H₂O, dried over Na₂SO₄ and stripped. Formation of the .HCl salt in abs EtOH-EtOAc in the usual manner gave Io as a white solid (0.188 g). Recrystallization from abs. EtOH afforded analytical material; mp 274°–275° (d).

Anal. calc'd. for C₂₄H₂₉N₃O₄.HCl: C, 62.67; H, 6.57; N, 9.14.

Found: C, 62.79; H, 6.46; N, 9.13.

We claim:

1. A compound having the formula

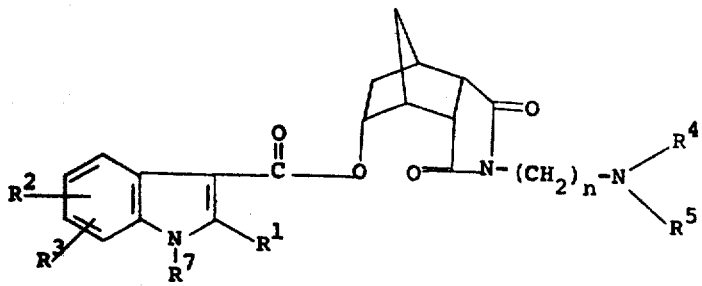

wherein R¹ is H, Cl, Br, F or (lower)alkyl, R⁷ is H or methyl, R² and R³ are alike or different and each is H, Cl, Br, F, (lower)alkyl, nitro, CF₃, OH or (lower)alkoxy, n is an integer of 2 to 4 inclusive and R⁴ and R⁵ are alike or different and each is H, (lower)alkyl or when taken together with the nitrogen a radical of the formula

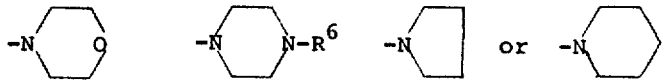

in which R⁶ is (lower)alkyl; or a pharmaceutically acceptable acid addition salt thereof.

2. A compound having the formula

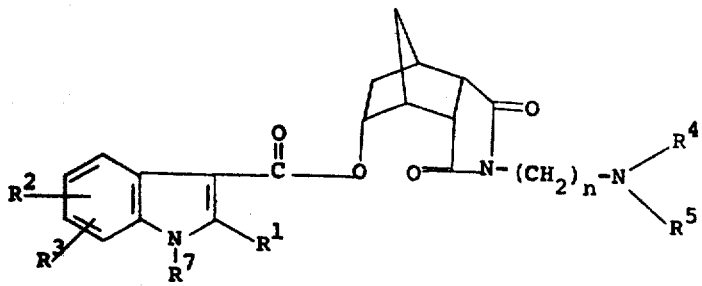

wherein R¹ is H, Cl, Br, F or (lower)alkyl, R⁷ is H or methyl, R² and R³ are alike or different and each is H, Cl, Br, F, (lower)alkyl, nitro, CF₃, OH or (lower)alkoxy, n is an integer of 2 to 4 inclusive and R⁴ and R⁵ are alike or different and each is H, (lower)alkyl or when taken together with the nitrogen a radical of the formula

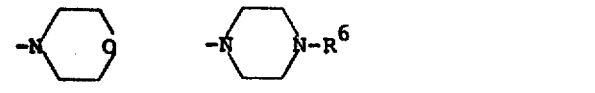

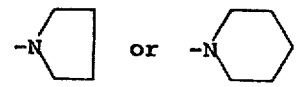

in which R⁶ is (lower)alkyl; or a pharmaceutically acceptable acid addition salt thereof.

3. A compound of claim 2 having the formula

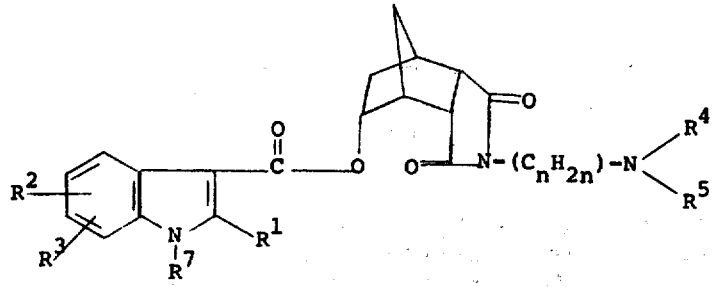

I

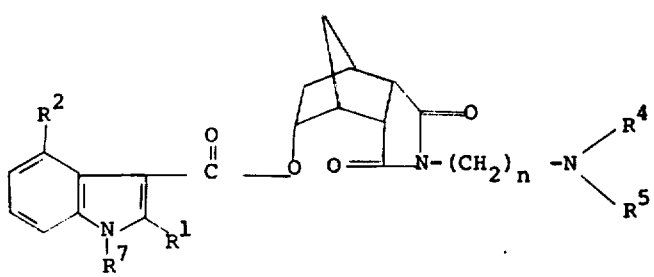

wherein $R^1$ is Cl, Br, F, H or (lower)alkyl, $R^7$ is H or methyl, $R^2$ is H, Cl, Br, F, $CF_3$, (lower)alkyl, OH or (lower)alkoxy, n is an integer of 2 to 4 inclusive and $R^4$ and $R^5$ are alike or different and each is H, (lower)alkyl or when taken together with the nitrogen radical of the formula

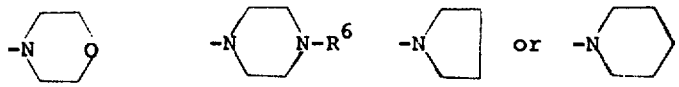

in which $R^6$ is (lower)alkyl; or a pharmaceutically acceptable acid addition salt thereof.

4. A compound of claim 2 having the formula

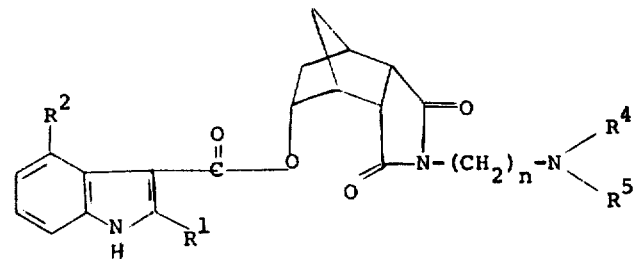

wherein $R^1$ and $R^2$ are alike or different and each is H, Cl, Br, F, or (lower)alkyl, and $R^2$ can also be $CF_3$, n is an integer of 2 to 4 inclusive and $R^4$ and $R^5$ are like or different and each is H, (lower)alkyl or when taken together with the nitrogen a radical of the formula

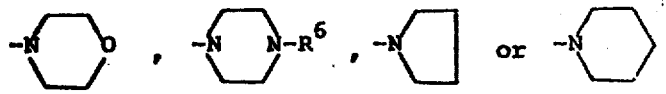

in which $R^6$ is (lower)alkyl; or a pharmaceutically acceptable acid addition salt thereof.

5. A compound of claim 2 having the formula

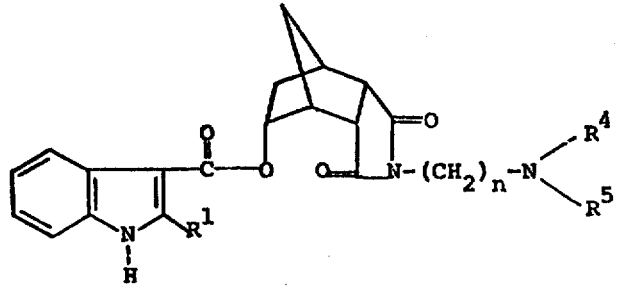

wherein $R^1$ is H, F, Cl, methoxy, ethoxy or n-propoxy, n is an integer of 2 to 4 inclusive and $R^4$ and $R^5$ are alike or different and each is H, (lower)-alkyl or when taken together with the nitrogen a radical of the formula

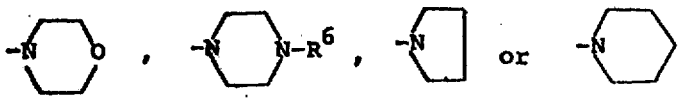

in which $R^6$ is (lower)alkyl; or a pharmaceutically acceptable acid addition salt thereof.

6. A compound of claim 2 having the formula

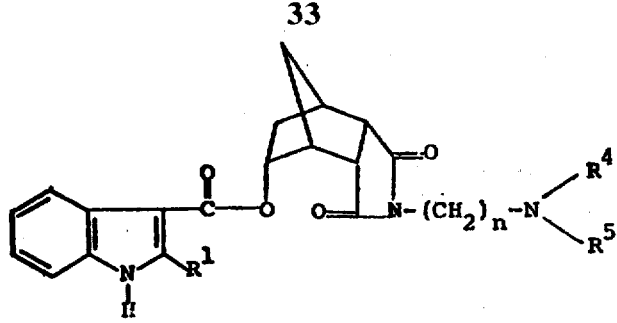

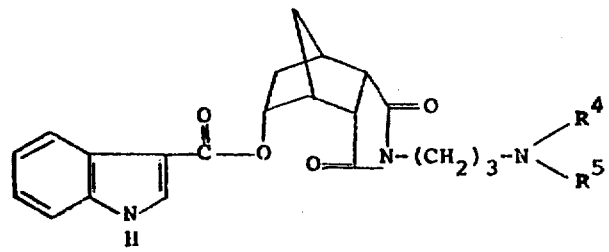

wherein $R^1$ is H, F, Cl, methoxy, ethoxy or n-propoxy, $n$ is an integer of 2 to 4 inclusive and $R^4$ and $R^5$ are alike or different and each is H or (lower)alkyl; or a pharmaceutically acceptable acid addition salt thereof.

7. A compound of claim 2 having the formula

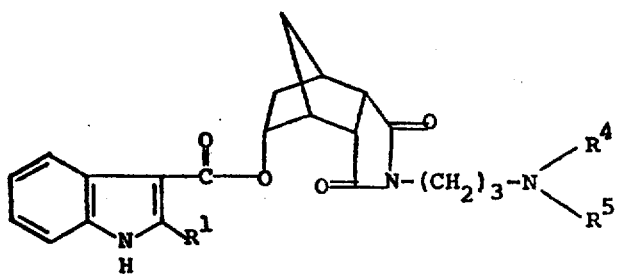

in which $R^1$ is H, Cl, methoxy or ethoxy, and $R^4$ and $R^5$ are alike or different and are H or (lower)alkyl; or a pharmaceutically acceptable acid addition salt thereof.

8. A compound having the formula

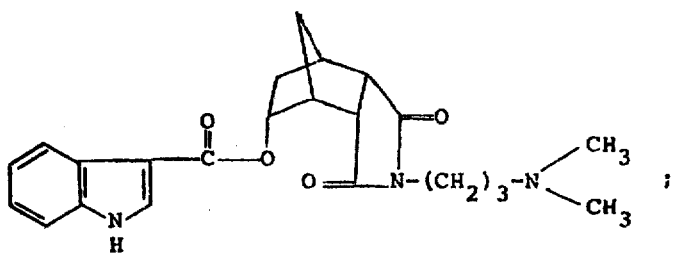

in which $R^4$ and $R^5$ are alike or different and each is H, methyl, ethyl or isopropyl; or a pharmaceutically acceptable acid addition salt thereof.

9. The compound having the formula or the hydrochloride salt thereof.

10. The compound having the formula

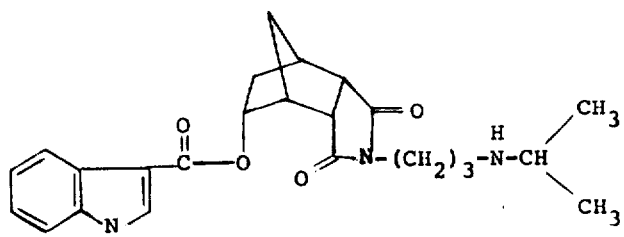

or the hydrochloride salt thereof.

11. The essentially pure levorotatory isomer of the compound of claim 9.

12. The essentially pure dextrorotatory isomer of the compound of claim 9.

13. The essentially pure dextrorotatory isomers of the compounds of claim 1.

14. The essentially pure levorotatory isomers of the compounds of claim 1.

15. The essentially pure levorotatory isomers of the compounds of claim 2.

16. The essentially pure dextrorotatory isomers of the compounds of claim 2.

17. The essentially pure levorotatory isomers of the compounds of claim 6.

18. The essentially pure dextrorotatory isomers of the compounds of claim 6.

* * * * *